US007129326B2

(12) United States Patent
Janssen et al.

(10) Patent No.: US 7,129,326 B2
(45) Date of Patent: Oct. 31, 2006

(54) METHODS FOR SELECTIVE TARGETING

(75) Inventors: Giselle G. Janssen, San Carlos, CA (US); Christopher J. Murray, Soquel, CA (US); Deborah S. Winetzky, Foster City, CA (US)

(73) Assignee: Genencor International, Inc., Palo Alto, CA (US)

( * ) Notice: Subject to any disclaimer, the term of this patent is extended or adjusted under 35 U.S.C. 154(b) by 69 days.

(21) Appl. No.: 10/303,331

(22) Filed: Nov. 25, 2002

(65) Prior Publication Data

US 2003/0152976 A1 Aug. 14, 2003

Related U.S. Application Data

(63) Continuation-in-part of application No. 09/832,723, filed on Apr. 11, 2001, now abandoned.

(60) Provisional application No. 60/197,259, filed on Apr. 14, 2000.

(51) Int. Cl.
*C07K 7/00* (2006.01)
*G01N 33/53* (2006.01)

(52) U.S. Cl. ..................... 530/329; 530/300

(58) Field of Classification Search ............... 530/300, 530/329
See application file for complete search history.

(56) References Cited

U.S. PATENT DOCUMENTS

| | | | |
|---|---|---|---|
| 3,929,678 A | 12/1975 | Laughlin et al. ............ | 252/526 |
| 4,683,202 A | 7/1987 | Mullis ......................... | 435/91 |
| 4,760,025 A | 7/1988 | Estell et al. ................ | 435/222 |
| 4,800,197 A | 1/1989 | Kowcz et al. .............. | 514/162 |
| 5,011,681 A | 4/1991 | Ciotti et al. ................. | 424/81 |
| 5,061,620 A | 10/1991 | Tsukamoto et al. ........ | 435/7.21 |
| 5,270,181 A | 12/1993 | McCoy et al. ............. | 435/69.7 |
| 5,283,173 A | 2/1994 | Fields et al. ................... | 435/6 |
| 5,292,646 A | 3/1994 | McCoy et al. ............. | 435/69.7 |
| 5,475,096 A | 12/1995 | Gold et al. ................ | 536/23.1 |
| 5,582,981 A | 12/1996 | Toole et al. .................. | 435/6 |
| 5,605,793 A | 2/1997 | Stemmer ....................... | 435/6 |
| 5,665,539 A | 9/1997 | Sano et al. .................... | 435/6 |
| 5,677,136 A | 10/1997 | Simmons et al. .......... | 435/7.24 |
| 5,733,731 A | 3/1998 | Schatz et al. ................. | 435/6 |
| 5,750,397 A | 5/1998 | Tsukamoto et al. ......... | 435/372 |
| 5,837,500 A | 11/1998 | Ladner et al. ............. | 435/69.7 |
| 6,201,104 B1 * | 3/2001 | MacDonald et al. ........ | 530/327 |

FOREIGN PATENT DOCUMENTS

| | | |
|---|---|---|
| WO | WO 91/18980 | 12/1991 |
| WO | WO 91/19818 | 12/1991 |
| WO | WO 96/33010 | 10/1996 |
| WO | WO 96/41180 | 12/1996 |
| WO | WO 97/22617 | 6/1997 |
| WO | WO 97/35198 | 9/1997 |
| WO | WO 98/54312 | 12/1998 |
| WO | WO00/32631 | * 6/2000 |
| WO | WO01/79479 A2 | * 10/2001 |

OTHER PUBLICATIONS

Copy of sequence search alignment.*
Arap et al., "Cancer Treatment by Targeted Drug Delivery to Tumor Vasculature in a Mouse Model," *Science*, vol. 279, pp. 377-380, Jan. 1998.
Balass et al., "Recovery of High-Affinity Phage from a Nitrostreptavidin Matrix in Phage-Display Technology, *Analytical Biochemistry*," vol. 243, pp. 264-269, 1996.
Barbas et al., "Recent Advances in Phage Display," *Current Opinion in Biotechnology*, vol. 4, pp. 526-530, 1993.
Barrett et al., "Selective Enrichment and Characterization of High Affinity Ligands from Collections of Random Peptides on Filamentous Phage," *Analytical Biochemistry*, vol. 204, pp. 357-364, 1992.
Barry et al., "Toward cell-targeting gene therapy vectors: Selection of cell binding peptides from random peptide-presenting phage libraries," *Nature Medicine*, vol. 2, No. 3, pp. 299-305 Mar. 1996.
Bartoli, et al., "DNA-based selection and screening of peptide ligands," *Nature Biotechnology*, vol. 16, pp. 1068-1074, Nov. 1998.
Bayer et al., "Protein Biotinylation," *Methods in Enzymology*, vol. 184, pp. 138-161.
Boder et al., "Yeast surface display for screening cominatorial polypeptide libraries," *Nature Biotechnology*, vol. 15, pp. 553-557, Jun. 1997.
Cao et al., "Detecting and Identifying Active Compounds from a Combinatorial Library Using IAsys and Electrospray Mass Spectrometry," *Techniques in Protein Chemistry VIII, Ed. by Marshak*, pp. 177-184.
Chang et al., "Targeting of Phototoxic Drugs to Antigen-Specific T Lymphocytes *in vitro* Using Antigen-Presenting Cell Membranes," *Photochemistry and Photobiology*, vol. 61, No. 5, pp. 499-505, 1995.
Cheng et al., "Using Electrospray Ionization FICR Mass Spectrometry to Study Competitive Binding of Inhibitors to Carbonic Anhydrase," *J. Am. Chem. Soc.*, vol. 117, pp. 8859-8860, 1995.
Christian et al., "Simplified Methods for Construction, Assessment and Rapid Screening of Peptide Libraries in Bacteriophage," *J. Mol. Biol.* vol. 227, p. 711-718, 1992.
Cull et al., "Screening for receptor ligands using large libraries of peptides linking to the C terminus of the *lac* repressor," *Proc. Natl. Acad. Sci, USA*, vol. 89, pp. 1865-1869, Mar. 1992.

(Continued)

*Primary Examiner*—Peter Paras, Jr.
*Assistant Examiner*—My-Chau T Tran
(74) *Attorney, Agent, or Firm*—Genencor International, Inc.

(57) ABSTRACT

A selective targeting method is disclosed which comprises contacting a peptide library with an anti-target to allow the peptides to bind; separating non-binding peptides from the anti-target bound peptides, contacting the non-binding anti-target peptides with a target allowing the unbound peptides to bind with the target to form a target-bound peptide complex; separating the target-bound peptide complex from peptides which do not bind to the target, and identifying the target-bound peptides. In one embodiment the target is skin or hair. In another embodiment the anti-target is hair when the target is skin, and the anti-target is skin when the target is hair.

1 Claim, 2 Drawing Sheets

OTHER PUBLICATIONS

Cwirla et al., "Peptides on phage: A vast library of peptides for identifying ligands," *Proc. Natl. Acad. Sci. USA*, vol. 87, pp. 6378-6382, Aug. 1990.

de Bruin et al., "Selection of high-affinity phage antibodies from phage display libraries," *Nature Biotechnology*, vol. 17, pp. 397-399, Apr. 1999.

Devlin et al., "Random Peptide Libraries: A Source of Specific Protein Binding Molecules," *Science*, vol. 249, pp. 404-406, Jul. 1990.

Evans et al., "Design of Nonpeptidal Ligands for a Peptide Receptor: Cholecystokinin Antagonists," *J. Med. Chem.*, vol. 5, No. 5, pp. 1359-1364, Dec. 1999.

Ferrara et al., "Clinical applications of angiogenic growth factors and their inhibitors," *Nature Medicine*, vol. 5, No. 5, pp. 1359-1364, Dec. 1999.

Fodor et al., "Light-Directed, Spatially Addressable Parallel Chemical Synthesis," *Science*, vol. 251, pp. 767-773, Feb. 1991.

Gao et al., "Screening Derivatized Peptide Libraries for Tight Binding Inhibitors to Carbonic Anhydrase II by Electrospray Ionization-Mass Spectrometry," *J. Med. Chem.*, vol. 39, pp. 1949-1955, 1996.

Gerber et al., "VEGF couples hypertrophic cartilage remodeling, ossification and angiogenesis during endochondral bone formation," *Nature Medicine*, vol. 5, No. 6, pp. 623-628, Jun. 1999.

Griffin et al., "The discovery and characterization of a novel nucleotide-based thrombin inhibitor," *Gene*, vol. 137, pp. 25-31, 1993.

Gubler et al., "A simple and very efficient method for generating cDNA libraries," *Gene*, vol. 25, pp. 263-269, 1983.

Hajduk et al., "High-Throughput Nuclear Magnetic Resonance-Based Screening," *J. Med. Chem.*, vol. 42, pp. 2315-2317, 1999.

Hanes et al., "*In Vitro* selection and evolution of functional proteins by using ribosome display," *Proc. Natl. Acad. Sci. USA*.

Huls et al., "A recombinant, fully human monoclonal antibody with antitumor activity constructed from phage-displayed antibody fragments," *Nature Biotechnology*, vol. 17, pp. 276-281, Mar. 1999.

Klumb et al., "Energetic Roles of Hydrogen Bonds at the Ureido Oxygen Binding Pocket in the Streptavidin-Biotin Complex," *Biochemistry*, vol. 37, No. 21, pp. 7657-7663, May 26, 1998.

Koivunen et al., "Tumor targeting with a selective gelatinase inhibitor," *Nature Biotechnology*, vol. 17, pp. 768-774, Aug. 1999.

Lam et al., "The Chemical Synthesis of Large Random Peptide Libraries and Their Use for the Discovery of Ligands for Macromolecular Acceptors," *Bioorganic & Medicinal Chemistry Letters*, vol. 3, No. 3, pp. 419-424, 1993.

Lenstra et al., "Isolation of sequences from a random-sequence expression library that mimic viral epitopes," *J. of Imunological Methods*, vol. 152, pp. 149-157, 1992.

Marshall et al., "Fourier Transform Ion Cyclotron Resonance Mass Spectrometry: A Primer," *Mass Spectrometry Reviews*, vol. 17, pp. 1-35, 1998.

Morton et al., "Kinetic Analysis of Macromolecular Interactions Using Surface Plasmon Resonance Biosensors," *Methods in Enzymology*, vol. 295, pp. 268-294, 1998.

Nelson et al., Advances in surface plasmon resonance biomoleculr interaction analysis mass spectrometry (BIA/MS), *J. Molecular Recognition*, vol. 12, pp. 77-93, 1999.

Parmley et al., "Antibody-selectable filamentous fd phage vectors: affinity purification of target genes," *Gene*, vol. 73, pp. 305-318, 1988.

Pinilla et al., "Investigation of antigen-antibody interactions using a soluable, non-support-bound synthetic decapeptide library composed of four trillion ($4 \times 10^{12}$) sequences," *Biochem. J.*, vol. 301, pp. 847-853, 1994.

Reineke et al., "A synthetic mimic of a discontinuous binding site on interleukin-10," *Nature Biotechnology*, vol. 17, pp. 271-275.

Sambrook, J. et al., *Molecular Cloning, A Laboratory Manual*, 2nd Ed., Cold Spring Harbor Laboratory Press, Chapter 1: "Plasmid Factors" 1989.

Sambrook, J. et al., *Molecular Cloning, A Laboratory Manual*, 2nd Ed., Cold Spring Harbor Laboratory Press, Chapter 16: "Expression of Cloned Genes in Cultured Mammalian Cells" 1989.

Scott et al., "Searching for Peptide Ligands with an Epitope Library," *Science*, vol. 249, pp. 386-390, Jul. 1990.

Singleton et al., *Dictionary of Microbiology and Molecular Biology*, 2nd Ed., pp. 34-37.

Smith, G.P., "Filamentous Fusion Phage: Novel Expression Vectors That Display Cloned Antigens on the Virion Surface," *Science*, vol. 228, pp. 1315-1317, Jun. 1985.

Smith, G.P. et al., "Libraries of Peptides and Proteins Displayed on Filamentous Phage," *Methods in Enzymology*, vol. 217, pp. 228-257, 1993.

Smith, M., "In Vitro Mutagenesis," *Ann. Rev. Genet.*, vol. 19, pp. 423-462, 1985.

Szabo et al., "Surface plasmon resonance and its use in biomolecular interaction analysis (BIA)," *Structural Biology*, vol. 5, pp. 699-705, 1995.

Tjoeng et al., "Multiple peptide synthesis using a single support (MPS3)," *Int. J. Peptide Protein*, vol. 35, pp. 141-146, 1990.

Tuerk et al., "Systematic Evolution of Ligands by Exponential Enrichment: RNA Ligands to Bacteriophage T4 DNA Polymerase," *Science*, vol. 2, pp. 505-510, Aug. 1990.

Walk et al., "ESI Fourier Transform Ion Cyclotron Resonance Mass Spectrometry, (ESI-FT-ICR-MS): A Rapid High-Resolution Analytical Method for Combinatorial Compound Libraries," *Angew. Chem. Int. Ed.*, vol. 38, No. 12, pp. 1763-1765, 1999.

Wu et al., "Quantitative electrospray mass spectrometry for the rapid assay of enzyme inhibitors," *Chemistry & Biology*, vol. 4, No. 9, pp. 653-657, 1997.

Youngquist et al., "Generation and Screening of Combinatorial Peptide Libraries Designed for Rapid Sequencing by Mass Spectrometry," *J. Am. Chem. Soc.*, vol. 117, p. 3900-3906, 1995.

Xiang et al., "A Combinatorial Approach to Materials Discovery," *Science*, vol. 268, pp. 1738-1742, Jun. 1995.

* cited by examiner

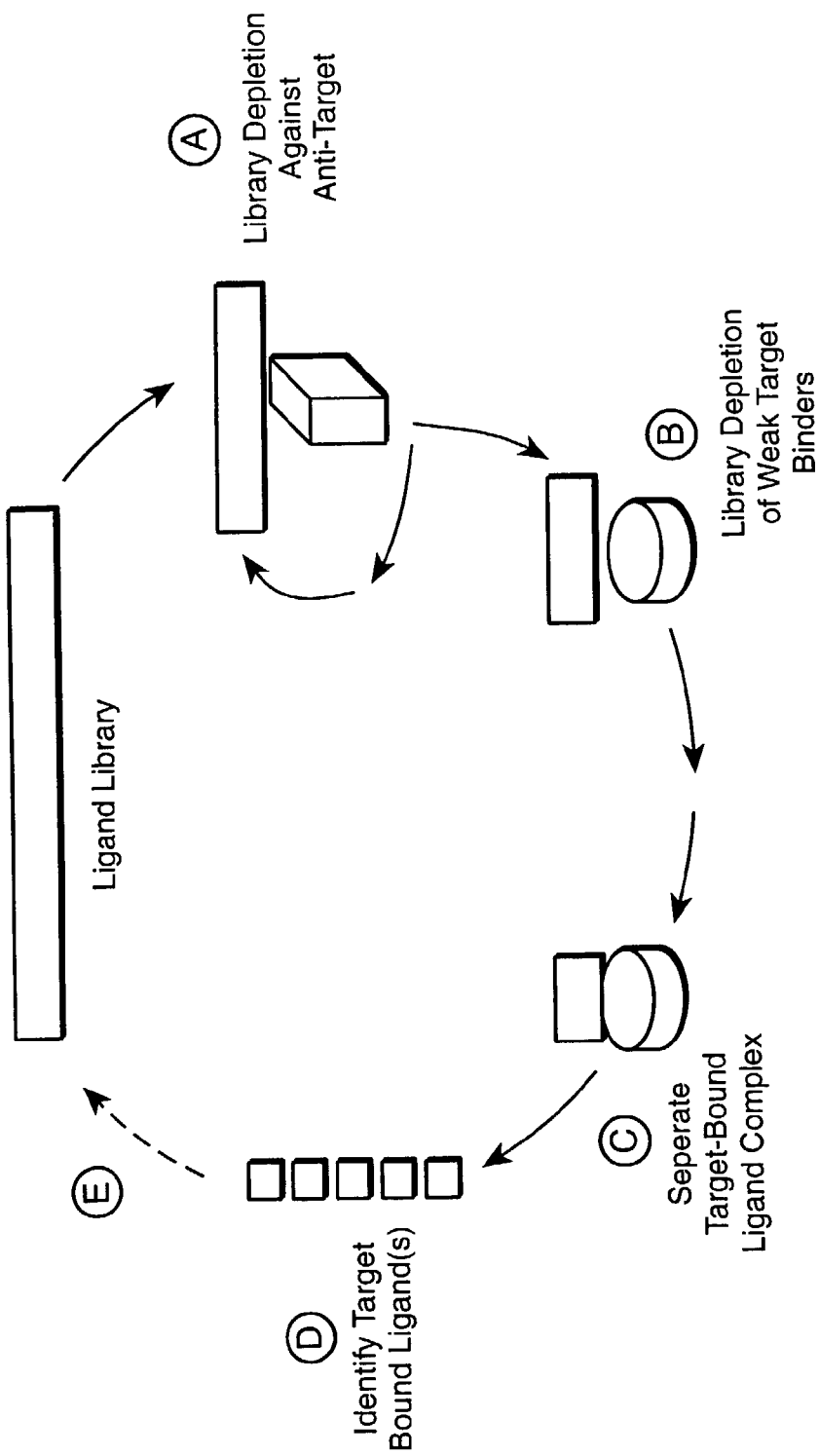
FIG._1

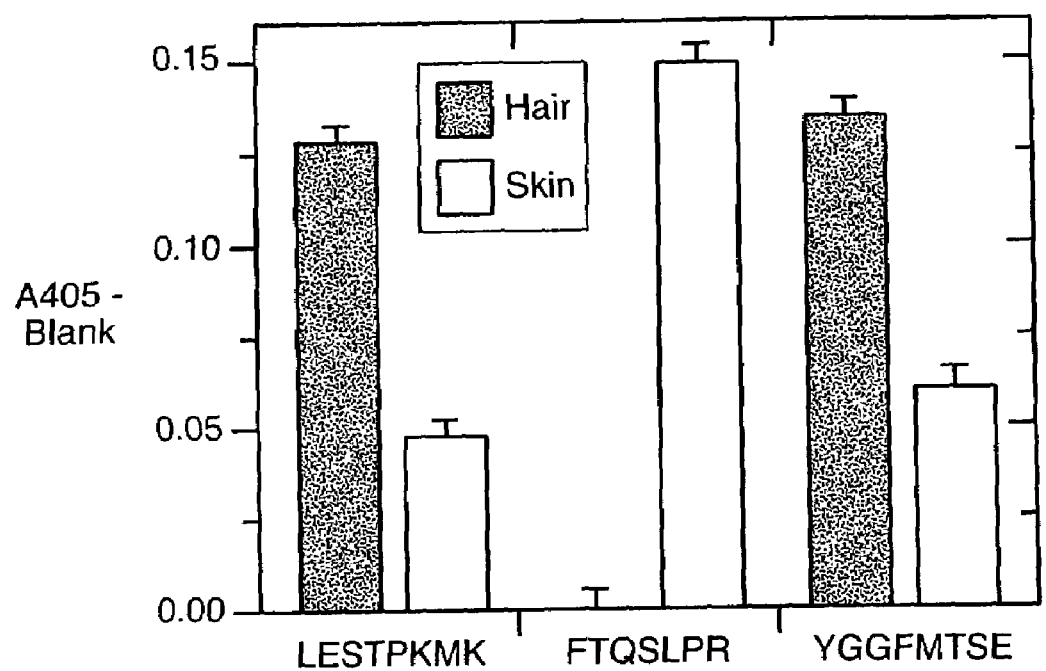
FIG._2

METHODS FOR SELECTIVE TARGETING

This is a continuation-in-part of application Ser. No. 09/832,723, filed Apr. 11, 2001 now abandoned.

CROSS-REFERENCE TO RELATED APPLICATIONS

Pursuant to 35 U.S.C. § 120 and 35 U.S.C. §119(e), the present application claims the benefit of and priority to U.S. Ser. No. 09/832,723, filed Apr. 11, 2001, now abandoned, and U.S. Ser. No. 60/197,259, filed Apr. 14, 2000, both applications entitled "Methods For Selective Targeting", by Murray et al.

BACKGROUND OF THE INVENTION

The present invention is directed to methods for the selection and identification of compounds capable of binding specifically to a target in the presence of undesired background targets (anti-targets) using libraries of similar compounds. In one particular aspect, the present invention is related to the selection of ligands from peptide libraries. Ligand peptides identified according to the method of the invention may have a binding affinity and a selectivity to a target similar to the binding affinity and selectivity of antibodies.

The literature is replete with examples of recent advances in methods for screening large library pools of compounds, especially peptides. Methods for screening these compounds to identify molecules that bind to a preselected target have also been advanced. One well-known method is biopanning which was originally developed by Smith, G.P., (1985), *Science* 228:1315. Biopanning in its simplest form is an in vitro selection process in which a library of phage-displayed peptides is incubated with a target. The target and phage are allowed to bind and unbound phage are washed away. The specifically bound phage are then acid eluted. The eluted pool of phage is amplified in vivo and the process is repeated. After a number of rounds individual clones are isolated and sequenced.

A number of variations of the biopanning technique first introduced by Smith have been described, and reference is made to Christian et al., (1992) *J. Mol. Biol.*, 227:711; Cwirla et al., (1990) *Proc. Natl. Acad. Sci. USA*, 87:6378; Cull et al., (1992) *Proc. Natl. Acad. Sci. USA*, 89:1865; Huls et al., (1996) *Nature Biotechnol.*, 7:276; and Bartoli et al., (1998) *Nature Biotechnol.*, 16:1068.

Huls et al., 1996 supra, describe a method comprising flow cytometry-based subtractive selection of phage antibody on intact tumor cells. The phage-displayed antibodies remain bound to the target during the flow-cytometric selection. However, prior to amplification the cell-bound phages are eluted from the target. WO 98/54312 discloses selection of antibodies under mild conditions with high affinities for antigens using antibody libraries displayed on ribosomes.

In many prior art methods it is generally assumed that elution of target bound ligands is sufficient to identify the tightest binding ligands in a library. However, a number of research papers report on low affinity binders using elution techniques (U.S. Pat. No. 5,582,981). Nevertheless, physical separation of the ligands from the target prior to amplification or identification is the standard method for selecting ligands that bind to a preselected target.

Balass et al., (1996) *Anal. Biochem.*, 243:264, describe the selection of high-affinity phage-peptides from phage-peptide libraries using a biotinylated target immobilized on a nitrostreptavidin matrix. The interacting phage particles were released under conventional acid elution. Further, after acid elution, the target complex was analyzed for bound phage. These particles were exposed to alkaline solutions or free biotin to release the target bound phage particles from the solid support. The affinity of the isolated phage was found to be higher than the phage released by traditional acid elution methods. However, the synthetically prepared peptides exhibited a lower affinity for the target than the peptides prepared from sequences obtained by acid-eluted phage.

Other targeting methods include, for example, SELEX. This is a procedure in which an oligonucleotide from a library of randomized sequences is embedded in a pool of nucleic acids. Many cycles of affinity selection to a target of the oligonucleotide from the heterologous RNA or DNA population occurs. The target and annealed nucleic acids are partitioned and amplified. In order to proceed to the amplification step, selected nucleic acids must be released from the target after partitioning. (U.S. Pat. No. 5,475,096)

While various methods for screening and selecting libraries of compounds exist, improved methods that do not require multiple rounds of selection are particularly needed for compounds that a) bind tightly and specifically to targets that are not well-defined at the chemical, biochemical or genetic level but have macroscopic properties that are desirable to target, b) bind tightly and specifically to targets that cannot be easily physically separated from a large background of undesirable targets (anti-targets), and c) bind to targets under harsh conditions, such as acidic pH, high detergent concentration or high temperature.

The selective targeting method according to the invention overcomes some of the above deficiencies of the prior art methods and in particular offers an advantage in rapidly identifying compounds, particularly peptides, that bind with a high affinity and selectively to a target.

SUMMARY OF THE INVENTION

In one aspect, the invention concerns a method for screening a ligand library, particularly a peptide library comprising contacting the ligand library with an anti-target to allow the ligands to bind with the anti-target; separating unbound ligands and contacting said unbound ligands with the selected target to allow said unbound ligands to bind with the target to form a target-bound ligand complex; separating said target-bound ligand complex from ligands which do not bind to said target; and identifying the target-bound ligands on the target-bound ligand complex.

In a second aspect, the invention concerns a method for screening a ligand library, particularly a peptide library comprising contacting the ligand library essentially simultaneously with a selected target and an anti-target to allow the ligands to bind with the target forming a target-bound ligand complex; separating the target-bound ligand complex from the anti-target, anti-target bound ligands and free ligands; and identifying the ligands of the target-bound ligand complex. The contacting step may be accomplished either in vivo or in vitro.

In one embodiment, the anti-target is skin and the target is hair. In a second embodiment, the anti-target is hair and the target is skin. In a third embodiment, the ligand is a peptide but not an antibody.

BRIEF DESCRIPTION OF THE DRAWINGS

FIG. 1 is a general schematic diagram of the selective targeting method disclosed herein. The method comprises the steps of, a) selection against anti-targets which provides a library of ligands depleted of anti-target bound ligands, b) selection for the target by formation of a target-bound ligand complex, c) separation of the target-bound ligand complex, d) identification of the target-bound ligands, and e) optionally sequencing the target-bound ligands, exposing the target-bound ligands to additional rounds of selective targeting, and/or diversification.

FIG. 2 illustrates enzyme-linked binding assay results for 2 peptides; LESTPKMK (SEQ ID NO. 115) which selectively targets hair and FTQSLPR (SEQ ID NO. 116) which selectively targets skin (■ depicts hair and ☐ depicts skin).

DETAILED DESCRIPTION OF THE INVENTION

A. Unless defined otherwise, all technical and scientific terms used herein have the same meaning as commonly understood by one of ordinary skill in the art to which this invention pertains. For the purposes of the present invention, the following terms are used to describe the invention herein.

The term "ligand" refers to a molecule or compound that is recognized by a particular target or anti-target. The term is independent of molecular size or compositional feature. The ligand may serve as a substrate for an enzyme-catalyzed reaction, as an agonist, as an antagonist, act as a signal messenger, or stimulate or inhibit metabolic pathways. Ligands may be nucleic acids, peptides, peptide derivatives, peptidomimetics, polypeptides, small organic molecules, carbohydrates and other molecules that are isolated from a candidate mixture that acts on a target in a desirable manner. Preferably the desirable manner is binding the target, but could include for example, catalytically changing the target or reacting with the target that modifies or alters the target.

The term "library" refers to a collection of chemical or biological entities that can be created in a single reservoir and simultaneously screened for a desired property. As used herein a library can have a minimum size of at least two members and may contain as many as $10^{15}$ members or more. In one aspect, the library has at least $10^2$ members. In another aspect, the library has at least $10^3$ members. In yet another aspect, the library has at least $10^6$ members. In a further aspect, the library has at least $10^9$ members. The size of a library refers to the total number of entities comprising the library whether the members are the same or different.

A "peptide library" refers to a set of peptides and to the peptides and any fusion proteins containing those peptides. Stochastic or random processes may be used to construct random peptides. The term "random" does not mean that the library composition is not known.

The term "peptide" refers to an oligomer in which the monomeric units are amino acids (typically, but not limited to L-amino acids) linked by an amide bond. Peptides may be two or more amino acids in length. Peptides identified according to the invention are preferably less than 50 amino acids in length, more preferably less than 30 amino acids in length, also preferably less than 25 amino acids in length, and preferably less than 20 amino acids in length. In one embodiment the peptides identified according to the method of the invention are between 4 and 20 and also between 6 and 15 amino acids in length. However, in general peptides may be up to 100 amino acids in length. Peptides that are longer than 100 amino acids in length are generally referred to as polypeptides. Standard abbreviations for amino acids are used herein. (See Singleton et al., (1987) *Dictionary of Microbiology and Molecular Biology*, Second Ed., page 35, incorporated herein by reference).

The peptides or polypeptides may be provided as a fusion peptide or protein. Peptides include synthetic peptide analogs wherein the amino acid sequence is known. The term peptide does not include molecules structurally related to peptides, such as peptide derivatives or peptidomimetics whose structure cannot be determined by standard sequencing methodologies, but rather must be determined by more complex methodologies such as mass spectrometric methods. Peptidomimetics (also known as peptide mimetics) are peptide analogs but are non-peptide compounds. Usually one or more peptide linkages are optionally replaced. (Evans et al., (1987) *J. Med. Chem.* 30:1229). The term "protein" is well known and refers to a large polypeptide.

A "skin or hair binding peptide" according to the invention is a peptide that binds to a target with a binding affinity of at least about $10^{-2}$ M, at least about $10^{-3}$ M, at least about $10^{-4}$ M, at least about $10^{-5}$ M, at least about $10^{-7}$ M, at least about $10^{-9}$ M, and preferably between about $10^{-2}$ M to $10^{-15}$ M, between about $10^{-2}$ M to $10^{-10}$ M, between about $10^{-3}$ M to $10^{-9}$ M and between $10^{-7}$ to $10^{-15}$ M.

The term "nucleic acid" means DNA, RNA, single-stranded or double-stranded and chemical modifications thereof. Modifications may include but are not limited to modified bases, backbone modifications, methylations, unusual base pairing modifications, and capping modifications. When a nucleic acid library is used in the selective targeting method of the invention, the nucleic acid ligand is generally between 4 and 250 nucleotides in length, and preferably between 4 and 60 nucleotides in length.

The invention further includes ligands, preferably nucleic acid, peptide or polypeptide ligands and more preferably peptide ligands that have substantially the same ability to bind to a target as the nucleic acid, peptide or polypeptide identified by the selective targeting method described herein. Substantially the same ability to bind a target means the affinity and selectivity is approximately the same as the affinity and selectivity of the ligands selected by the method herein claimed.

Additionally a ligand having substantially the same ability to bind to a target will be substantially homologous to the ligand identified by the disclosed selective targeting method. With respect to a nucleic acid sequence, substantially homologous to an identified ligand means the degree of primary sequence homology is in excess of 80%, preferably in excess of 85%, more preferably in excess of 90%, further preferably in excess of 95%, even more preferably in excess of 97%, and most preferably in excess of 99%. It will be appreciated by those skilled in the art that as a result of the degeneracy of the genetic code, a multitude of peptide encoding nucleotide sequences may be produced. A peptide or polypeptide is substantially homologous to a reference peptide or polypeptide if it has at least 50%, at least 60%, at least 65%, at least 70%, at least 75%, at least 80%, at least 85%, at least 90% and at least 95% sequence identity to the reference sequence when optimally aligned. Optimal alignment of the sequences may be conducted by various known methods and computerized implementation of known algorithms (e.g. TFASTA, BESTFIT, in the Wisconsin Genetics Software Package, Release 7.0, Genetics Computer Group, Madison, Wis.). General categories of equivalent amino acids include 1) glutamic acid and aspartic acid; 2) lysine, arginine, and histidine; 3) alanine, valine, leucine, and isoleucine; 4) asgaragine and glutamine; 5) threonine and serine; 6) phenylalaine, tyrosine and tryptophan; and 7) glycine and alanine. It is well within the ordinary skill of those in the art to determine whether a given sequence substantially homologous to those identified herein have substantially the same ability to bind a target.

A small organic molecule as defined herein is a molecule, preferably a nonpolymeric molecule, having a molecular weight of approximately 1000 Daltons or less and more preferably 500 Daltons or less. A "peptoid" is defined herein as an enzymatically resistant peptide analog.

The term "target" or "anti-target" refers to molecules or heterogeneous molecules that have a binding affinity as defined herein, for a given ligand. Both target and anti-targets may be naturally occurring or synthetic molecules or heterogeneous molecules. In a preferred embodiment, the target is skin or hair. Further when the target is skin, the anti-target is hair, and when the target is hair, the anti-target is skin.

The binding affinity of a ligand for its target or anti-target may be described by the dissociation constant ($K_D$), concentration needed for 50% effective binding ($EC_{50}$), or concentration needed for 50% inhibition of binding of another compound that binds to the target ($IC_{50}$). $K_D$ is defined by $k_{off}/k_{on}$. The $k_{off}$ value defines the rate at which the target-ligand complex breaks apart or separates. This term is sometimes referred to in the art as the, kinetic stability of the target-ligand complex or the ratio of any other measurable quantity that reflects the ratio of binding affinities, such as an enzyme-linked immunosorbent assay (ELISA) signal or radio-active label signal. Selectivity is defined by the ratio of binding affinities or $k_{off}$ for dissociation of the ligand-complex.(target $K_D$/anti-target $K_D$). The $k_{on}$ value describes the rate at which the target and ligand combine to form the target-ligand complex.

The term "contacting" is broadly defined to mean placing a library of ligands and a target or anti-target in immediate proximity or association and includes in vitro and in vivo contact. The term includes touching, associating, joining, combining, intravenous injection, oral administration, intraperitoneally, topical application, intramuscular, inhalation, subcutaneous application and the like. The term "separating" as used herein means to select, segregate, partition, isolate, collect, keep apart and disunite.

"Amplifying" means a process or combination of process steps that increases the amount or number of copies of a molecule or class of molecules. In one aspect, amplification refers to the production of additional copies of nucleic acid sequences that is carried out using polymerase chain reaction (PCR) technology well known in the art. In another aspect, amplification refers to production of phage virions by infection of a host.

As used in the specification and claims, the singular "a", "an" and "the" include the plural references unless the context clearly dictates otherwise. For example, the term "a ligand" may include a plurality of ligands.

The following references describe the general techniques employed herein: Sambrook et al., (1989) *Molecular Cloning: A Laboratory Manual*, Cold Spring Harbor Laboratory Press, Cold Spring Harbor, N.Y.; Innis et al., *PCR Protocols—A Guide to Methods and Applications* (1990), Academic Press, Inc.; Kay et al., (1996) *Phage Display of Peptides and Proteins*, Academic Press; Ausubel et al., (1987) *Current Protocols in Molecular Biology*, Greene-Publishing & Wiley Interscience NY (Supplemented through 1999); Berger and Kimmel, (1987) *Methods in Enzymology*, Vol. 152. Academic Press Inc., San Diego, Calif.

The contents of all references, patents and published patent applications cited throughout this application are hereby incorporated by reference in their entirety.

B. General Method

Described herein is a selective targeting method for screening a library of ligands having a binding affinity and selectivity for a selected target. In its most basic form the selective targeting method may be defined as follows: Preparing or obtaining a library of ligands, preferably peptides of different sequences and more preferably a random peptide library. Deselecting ligands that bind with an anti-target by contacting the ligand library with an anti-target under conditions favorable for binding between the ligands of the library and the anti-target; allowing the anti-target to bind with the ligands; and separating the anti-target non-binders (unbound ligands) from the anti-target ligand bound molecules and any free ligands. Contacting the anti-target non-binders with a selected target under suitable conditions and allowing them to bind. Ligands with an affinity for the target will bind to form a target-bound ligand complex. The removal of ligands bound to the anti-target and removal of weak target-bound ligands may generally be referred to as library depletion. The target-bound ligand complex is then separated from the remaining mixture including the unbound ligands, and the target-bound ligands are identified. The target-bound ligand complex or the target-bound ligands may then optionally be subjected to amplification, sequencing or further rounds of selection (FIG. 1). The invention further comprises the ligands identified according to the selective targeting method of the invention.

In the practice of the invention, a library of compounds to be tested will generally be provided. A library of ligands may include, but is not limited to, random peptide libraries, synthetic peptide or peptidomimetic combinatorial libraries, peptide loop libraries, combinatorial chemical libraries, and oligonucleotide libraries. These libraries are well known to those in the art as well as methods for making said libraries. Reference is made to Barbas, C. F. (1993) *Current Opinion in Biotech.*, 4:526; Cwirla et al., (1990) supra; Scott and Smith, (1990) *Science*, 249:386; Cull et al., (1992) supra; Pinilla et al., (1994) *Biochem. J.* 301:847; Sambrook et al., (1989) supra; Ausubel et al., (1987) supra; and Gubler and Hoffman, (1983) *Gene* 25:263; each of which is incorporated herein by reference.

One preferred type of library includes random peptide libraries (also sometimes referred to in the art as epitope libraries). These libraries may include cell-surface display libraries, for example yeast display (Boder and Wittrup (1997) *Nat. Biotechnol.*, 15:553); peptide libraries inserted into proteins (Lenstra et al., (1992) *J. Immunol. Methods*, 152:149 and U.S. Pat. No. 5,837,500); direct screening of peptides on polysomes (Tuerk et al., (1990) *Science* 249: 505) and phage display libraries (Delvin et al., (1990) *Science* 249:404; WO91/18980; Dower et al. WO91/19818; and Parmley et al., (1988) *Gene* 73:305). Phage display libraries are particularly preferred. A phage display library is a library in which numerous peptides are displayed on the surface of a bacteriophage, such as a filamentous phage. The peptide or protein is expressed as a fusion with a coat protein of the bacteriophage resulting in display of the fusion protein on the surface of the virion while the DNA encoding the fusion resides within the virion. Suitable non-limiting examples of vectors for construction of phage libraries include fAFF1; the fUSE series, such as fUSE5; lamba phage vectors; and T7 select (non-filamentous) phage vectors. (Smith and Scott (1993) *Methods Enzymol.* 217:228; and Cwirla et al., (1990) *Proc. Natl. Acad. Sci. USA* 87 :6378). Phag e-peptide library kits are available and reference is made to Chiron Corp. (Emeryville, Calif.), New England BioLabs Inc., Catalog No.8100 (Beverly, Mass.), and Novagen Catalog No. 70550-3 (Madison Wis.). While various antibody libraries are known, including antibody display libraries on phage (de Bruin et al., (1999) *Nat. Biotechnol.*, 17:397), in one preferred, aspect of the present invention, the library of ligands used in the selective targeting method according to the invention will not include antibodies.

Another type of peptide library encoded by nucleic acids includes a library wherein the peptide is expressed as a fusion with another protein, for example, either a cell-surface protein or an internal protein of a host. The nucleotides encoding the peptide are inserted into a gene encoding the internal protein. Various examples of this type of library include the fusion of peptides to a lac repressor, GAL4, thioredox in, and various antibodies (U.S. Pat. Nos. 5,283,173; 5,270,181; and 5,292,646). Cull et al. (1992) *Proc. Natl. Acad. Sci. USA* 89:1865 teach the construction of a fusion gene encoding a fusion protein of peptide library members and LacI. Nucleic acids encoding a library of peptides are inserted into a gene encoding LacI. The fusion protein and the fusion plasmid encoding the fusion protein are physically linked by binding of the peptides to the lac operator sequence in a plasmid. Host cells may be transformed with the library plasmids. The cells expressing the fusion protein are lysed releasing the fusion protein and associated DNA (see for example U.S. Pat. No. 5,733,731). The library can then be screened or selected. DNA shuffled libraries are also known which are constructed by homologous exchange of DNA fragments during DNA recombination methods or by synthetic methods (see for example U.S. Pat. No. 5,605,793 and Stemmer (1994), *Proc. Natl. Aca. Sci. USA* 91:10747).

So called anchor libraries have been described in PCT US96/09383 and WO 97/22617. This is a peptide library wherein peptides have non-continuous regions of random amino acids separated by specifically designated amino acids. These libraries are made by genetic or chemical means.

A combinatorial chemical library and particularly a peptide library may also be synthesized directly by methods known in the art including, but not limited to synthesis by arrays (Foder et al., (1991) *Science* 251:767); synthesis on solid supports (WO97/35198); and other chemical methods such as those disclosed in Lam et al., (1993) *Bioorg. Med. Chem. Lett.*, 3:419, Tjoeng et al., (1990) *Int. J. Pept. Protein Res.* 35:141, and WO96/33010.

Methods for creating combinatorial chemical libraries are also known in the art. Combinatorial libraries include large numbers of chemical variants for peptides, oligonucleotides, peptoids, carbohydrates, small organic molecules and even solid-state materials (Schultz et al., (1995) *Science*, 268: 1738). A core structure will be varied by adding substituents or by linking different molecular building blocks. Libraries may include molecules free in solution, linked to solid particles or beads, or arrayed on surfaces of modified organisms. Varying substituents around the core molecule may modify virtually any class of compounds. Various non-limiting examples of classes of compounds for combinatorial libraries include benzodiazepines; mercaptoacyl prolines; carbamates; chalcone libraries; ketoamide conjugates; polyketones; paclitaxel libraries; anilides; aryloxyphenoxypropionates; oxazolidinones; carbohydrates; and numerous other classes. While methods for making combinatorial libraries are well documented in the literature, these methods may be very time consuming. Various companies now make instrumentation to generate combinatorial libraries from both solution and solid phase synthesis (CombiChem Inc. (San Diego, Calif.); Advanced ChemTech (Louisville); Zymark Corp. (MA); and Hewlett Packard (CA)). Once a library has been generated it can optionally be purified for example by high performance liquid chromatography (HPLC). Once a small organic molecule is screened and identified according to the selective targeting method of the invention, it may be produced on a larger scale by means of organic synthesis known in the art.

As taught herein not only are standard methods for generating libraries of ligands well known, but also ligand libraries may be obtained commercially, for example from Sigma (St. Louis Mo.) or from various public sources such as American Type Culture Collection (ATCC) and the National Institute of Health (NIH).

Suitable targets and anti-targets used in the selective targeting method according to the invention include, but are not limited to, proteins, peptides, nucleic acids, carbohydrates, lipids, polysaccharides, glycoproteins, hormones, receptors, antigens, antibodies, viruses, pathogens, toxic substances, metabolites, inhibitors, drugs, dyes, nutrients, growth factors, cells or tissues.

Sources of cells or tissues include human, animal, bacterial, fungal, viral and plant. Tissues are complex targets and refer to a single cell type, a collection of cell types or an aggregate of cells generally of a particular kind. Tissue may be intact or modified. General classes of tissue in humans include but are not limited to epithelial, connective tissue, nerve tissue, and muscle tissue.

It is preferred that the target and anti-target are characterized in some detail at the structural, chemical or genetic level to allow some control over the purity, stability and concentration of the target. However, targets and anti-targets may be used that are not well characterized. Non-limiting examples of potentially not well-characterized targets include collar soil, tumor cells, human skin and hair.

In another aspect, when the target is damaged cells, tissue, or organs, the anti-target is healthy normal (non-damaged) cells, tissue, organs or combinations thereof. Specific non-limiting anti-target examples include healthy normal whole blood, skin, hair, teeth, and nails.

In some applications, the target and anti-target can be reversed depending upon the specific application of interest. For example there may be multiple applications where it is desirable to target human skin and not hair. Therefore the anti-target would be hair. In a similar application it may be desirable to target human hair and not the corresponding anti-target, skin.

The following general examples of target/anti-target used in the same application are provided for illustrative purpose only and are not meant to limit the selective targeting method disclosed herein: tumor cell/normal cell; receptor cell/cell not expressing the receptor; neoplastic cell/normal cell; soil stain/cotton fabric; food stain/ceramic; specific protease/other protease; serine protease/whole blood; hematopoietic stem cell/whole blood; specific enzyme variant/other forms of the enzyme; virus in a cell/cell; TNF-alpha/blood components; specific insect enzyme/homologous enzymes in animals; hematopoietic stem cell/other hematopoietic cells; hair/skin; nucleus/mitochondria; cytoplasm/nucleus; alpha/beta hydrolases/other hydrolases; and a specific enzyme involved in photosynthesis/leaf tissue.

Both the target and anti-target concentrations to be used in the selective targeting method will vary depending on the type of ligand library, anti-target and target used. As discussed herein, the disclosed method has wide applicability to many different targets and anti-targets, therefore the concentration useful in the method may vary from about 1.0 M to $10^{-15}$ M, preferably the concentration is in the $10^{-9}$ M range. In general an excess amount of anti-target relative to the amount of target is required. While not meant to limit the invention, this excess amount may be in the range of at least 10 fold greater to more than 1000 fold greater. An initial target concentration may be preferably provided in the range of $10^{-3}$ M to $10^{-15}$ M. In one embodiment, when the target is an enzyme, the target concentration may be provided in the range of about $10^{-3}$ M to $10^{-12}$ M. In another embodiment, when the target is a cytokine, the target may be provided in the concentration range of about $10^{-3}$ M to $10^{-12}$ M. In yet another embodiment, when the target is a hematopoietic cell, the target concentration may be provided in the range of about 10 to $10^9$ cells.

In certain preferred embodiments, the anti-target or target may be a material or surface, such as a fabric, ceramic, micro-fluidic chip, skin or hair. In this instance the area of the target or anti-target will be important. While not intended to limit the invention in any manner, in general the size of the anti-target or target material will be about 1.0 mm to 1.5 cm; more preferably about 25.0 mm to 0.5 cm; however, the diameter or area may be more or less than these values. While not meant to limit the invention, when human hair is a target or an anti-target the diameter of the hair strand may generally be between about 10 to 220 μm, between about 15 to 190 μm and between about 70 to 115 μm. When skin is a target or anti-target, typical skin swatches used in the disclosed method are between about 0.2 to 8.0 cm$^2$ and also between about 0.4 to 4.0 cm$^2$.

In one aspect, the invention is directed to the screening and identification of ligands that bind to a selected target to form a non-covalent target-ligand complex with a binding affinity in the range of antibody affinities for antigens. The ligand binding affinity according to the present invention for $K_D$, $EC_{50}$ or $IC_{50}$ is in the range of between about $10^{-2}$ M to $10^{-5}$ M, about $10^{-2}$ M to $10^{-10}$ M and about $10^{-7}$ M to $10^{-15}$ M, although higher or low binding affinities may be achieved. In one aspect, the binding affinity is in the range of at least about $10^{-2}$ M, at least about $10^{-3}$ M, at least about $10^{-4}$ M, at least about $10^{-5}$ M, at least about $10^{-7}$ M, at least about $10^{-9}$ M and also at least about $10^{-12}$ M. In another embodiment, the affinity is less than about $10^{-7}$ M. In another aspect, $k_{off}$ values for the ligand-target complex will be less than about $10^{-2}$ sec$^{-1}$, less than about $10^{-3}$ sec$^{-1}$, less than about $10^{-4}$ sec$^-$, and also less than about $10^{-5}$ sec$^{-1}$. The ligands identified according to the selective targeting method of the invention will not bind with any significance to the anti-target. While not meant to limit the invention, a preferred ligand identified according to the selective targeting method described herein may have a $K_D$ for the anti-target greater than about $10^{-4}$ M, and preferably greater than about $10^{-1}$ M.

The selective targeting method according to the invention may be characterized not only by the binding affinity of a ligand to the target, but also may be characterized by the selectivity of the ligand-target complex. The selectivity of ligand binding for a target compared to ligand binding to an anti-target can be defined by a ratio of $K_D$, $EC_{50}$ or $IC_{50}$ in the range of about 2:1 to 500:1. In one aspect, selectivity is at least about 2:1, at least about 3:1, at least about 5:1, at least about 10:1, at least about 20:1, at least about 30:1, at least about 50:1, and at least about 100:1.

In another aspect, the selective targeting method may be used to select ligands with a low affinity for the target but with a high selectivity for the target. In this aspect, the selectivity of ligand binding affinity for the target compared to said ligand binding to an anti-target would be at least about 2:1, at least about 3:1, at least about 5:1, at least about 10:1, also at least about 20:1, at least about 50:1, and even at least about 100: or greater. However, the target binding affinity would be in the range of about $10^{-2}$ M to $10^{-7}$ M, in the range of about $10^{-2}$ M to $10^{-5}$ and also in the range of about $10^{-2}$ M to $10^{-3}$.

Methods for measuring binding affinities and selectivity are well known in the art, and these methods include but are not limited to measurement by radio-labeled release and competition assay; by isothermal titration calorimetry; biosensor binding assays (Morton & Myszka, (1998) *Methods Enzymol.* 295:268–294); by fluorescence and chemi-luminescence spectroscopy; and by mass spectrophotometry (Gao et al., (1996), *J. Med, Chem.*, 39:1949).

In one aspect, the anti-target is combined with the library of ligands and allowed to incubate prior to exposing the library of ligands to the target. In another aspect, the anti-target and target are combined with the library of ligands essentially simultaneously. Essentially simultaneously means at the same time or very close in time wherein the ligand library is exposed to both the anti-target and the target prior to any separation step.

The selective targeting method as described herein may be performed in vitro or in vivo. When performed in vitro, the library of ligands and the anti-target (and optionally the target), are combined in or on a vessel. The vessel may be any suitable material or receptacle such as a plate, culture tube, micro titer plate, micro-fluidic chip, petri dish and the like.

Preferably, the anti-target and the target are available in an environment where non-specific binding events are minimized. This may be accomplished by various means including, but not limited to, 1) by coating a vessel containing the ligand library and the target/anti-target with BSA, skim-milk or other adsorbing protein to block non-specific binding, 2) by labeling the target molecule with a capture agent such as a biotinylated compound, for example biotin, avidin, or mutated form thereof which can be subsequently trapped by streptavidin or a streptavidin derivative, such as nitrostreptavidin, 3) displaying the target/anti-target on magnetic beads that can be physically separated from the library, or 4) by using library display vectors with low background adsorption properties. These methods are known in the art and reference is made to Parmley et al. (1988) supra; and Bayer et al., (1990) *Methods Enzymol.* 184:138.

A composition including a library of ligands and an anti-target may be combined together with additional compounds such as buffers and optionally detergents and organic solvents under suitable conditions to allow binding of the ligands with the anti-target. One skilled in the art is well aware of useful buffers. Non-limiting examples include; tris(hydroxymethyl)aminomethane (Tris) buffers; N-2-hydroxyethylpiperazine-N'-2-ethanesulfonic acid (HEPES) buffers; morphololino-ethanesulfonic acid (MES) buffers; buffered saline solutions, such as N,N-bis[2-hydroxyethyl] 2-aminoethanesulfonic acid (BES), Tris, and phosphate-buffered saline (PBS), preferably buffered saline solutions (Sambrook et al., (1989) supra). Commercial buffers are available for example SuperBlock™ (Pierce, Rockford, Ill.).

Other ingredients such as detergents, for example Tween and Triton can be used in the solutions.

Depending on the target, the composition including the ligand library and anti-target is incubated for a period of about 1 minute to about 96 hours to allow the ligands to bind with the anti-target. However, longer time periods may be used depending on the stability of the target, anti-target and ligand library. The component containing the unbound anti-target ligands is separated from the anti-target bound ligands after incubation. While not essential, the separated component including the unbound anti-target ligands may optionally be transferred to a new vessel including the anti-target, incubated and then the component containing the unbound anti-target ligands can again be separated from the bound anti-target ligands. This transfer process may be repeated numerous times, for example it may be repeated between 2 to 10 times or more. The repeated transfer step further reduces the number of ligands that bind to the anti-target. However, the contacting of the library of ligands with the anti-target and the separating of the anti-target bound ligands from the unbound ligands may be accomplished in one round. The contacting including incubation, and the separation steps, whether completed in one round or in multiple rounds may generally be referred to as deselection.

In general, the temperature conditions during deselection may be between 2 and 30° C. The temperature is limited by the stability of the components and is well within the skill of one of ordinary skill in the art to determine.

The unbound anti-target ligands may be separated from the anti-target bound ligands by methods well known in the art. Some of these methods include liquid transfer, washing, centrifugation, filtration, chromatography, micro-dissection and fluorescence activated cell sorting (FACS).

The ligand library, depleted of anti-target binding ligands and containing unbound ligands is transferred to a vessel including the target under suitable conditions which will allow one or more members of the ligand library to bind with the target thereby forming a target-bound ligand complex. In one aspect the ligands may be contacted with the same target. In another aspect the ligands may be contacted with an array of targets at the same time. One non-limiting example of an array of targets includes the contacting of a ligand with multiple stains on a surface. The ligands are incubated under conditions that allow binding to the target and generally for a period of time ranging from about 1 minute to about 96 hours. The incubation time depends on the stability of the target. When the target is a stain, the incubation period will generally range from about 5 minutes to about 90 minutes. The vessel may further include buffers as described herein above. The temperature range is generally between about 2 and 30° C., and preferably about 18 to 25° C.

One skilled in the art is well aware of references describing cell, organ, and tissue culture, and reference is made to Atlas and Parks (eds) (1993), *The Handbook of Microbiological Media*, CRC Press, Boca Raton Fla.; Gamborg and Phillips (eds) (1995) *Plant Cell Tissue and Organ Culture, Fundamental Methods*, Springer Lab Manual Springer-Verlag.

The target-bound ligand complex may be subject to one or more wash steps. The washing compounds may include buffers (such as TBS and PBS), detergents, acids (glycine), organic solvents, bases, enzymes, sonication, or combinations thereof, wherein unbound ligands are washed. When the target-bound ligand complex is subject to an acid elution, the pH of the acid elution may be in the range of about 1.5 to 4.5, preferably in the range of about 2.0 to 3.5. The acid elution may take place for between 2 to 20 minutes and generally no longer than about 10 minutes. The wash step may be repeated numerous times and in general can be repeated between 2–6 depending on the specific target and ligand library. Particularly when the washing step is with an acid, washing will generally be followed by neutralization with various well-known compounds and buffers, such as TRIS-HCL. The washing step results in a target-bound ligand complex comprising tight binding ligands having a $K_D$, $k_{off}$ and selectivity values as herein defined.

When the ligand library is contacted with the anti-target and target essentially simultaneously as opposed to sequentially, the ligand library, anti-target and target composition may further include all materials described above for the sequential exposure of the anti-target and target.

Further when the ligand library is contacted with the anti-target and target essentially simultaneously, the method may also be performed in vivo. In this aspect, the library of ligands may be administered by means well known in the art, but preferably by injection into a host. If the library is a phage-peptide library, the number of transducing units may be in the range of $10^4$–$10^{10}$. The host may be any animal, such as a human, mouse, chicken, or pig, preferably mouse. The target for example may be whole organs or damaged or tumor tissue, more specifically tumor blood vessels. If the target is a tissue or cells found in the blood, the library of ligands may be circulated in the blood for a period of about 1 minute to 10 minutes and allowed to bind with the target. The target-bound ligand complex may be recovered after perfusion and the tissue dissected (Koivunen et al., (1999) *Nature Biotech.* 17:768 and Arap et al., (1998) *Science* 279:377).

Separation of the target-bound ligands from the anti-target unbound ligands or free ligands in the mixture may also be accomplished by well-known means in the art and these methods include affinity chromatography; centrifugation; high-performance liquid chromatography (HPLC); filtration, such as gel filtration; enzyme-linked immunosorbent assays (ELISA); and fluorescence-activated cell sorting (FACS). The choice of the separating method will depend on various factors such as the target, anti-target and ligand molecules. The choice of the separation method is well within the skill of one in the art and a variety of instruments used for these separation methods are commercially available. (See Kenny and Fowell (eds) (1992) *Practical Protein Chromatography Methods in Molecular Biology*, vol. 11, Humana Press, Totowa N.J.).

The target-bound ligand on the target-bound ligand complex may be identified by various techniques including polymerase chain reaction (PCR), mass spectrophotometry (MS), surface plasmon resonance, immunoprecipitation and nuclear magnetic resonance (NMR) spectroscopy (U.S. Pat. No. 4,683,202; Szabo et al., (1995) *Curr. Opin. Struct. Bio.* 5:699; Harlow et al., (1999) *Using Antibodies, A Laboratory Manual*, Cold Spring Harbor Press; and Hajduk et al., (1999) *J. Med Chem.*, 42:2315). Asymmetric PCR may also be used for identification of the target-bound ligand wherein a single primer species or primers in differential concentration may be used. As well known to those in the art, when the library members are genetically linked to the peptide or protein, DNA or mRNA can be amplified by PCR and the corresponding sequence subcloned into a vector for sequencing and identification.

During the process of the identifying step, the target-bound ligand may separate from the target-bound ligand complex, but the identifying step does not require separation, and preferably the target-bound ligand is not separated from the target-bound ligand complex prior to identification of the ligand. For example, in mass spectrophotometry (MS), once the target-bound ligand complex is injected into the mass spectrophotometer the target-bound ligand may be separated from the target complex. Additionally, PCR may be directly carried out on the target-bound ligand complex.

The selective targeting method according to the invention preferably includes PCR to identify target-bound peptides. According to the invention use of PCR results in the recovery of peptides not recovered by conventional biopanning methods which utilize acid-elution. In general, a ligand encoding a DNA is amplified by PCR with appropriate primers.

The presence of specific PCR products indicates that the target-bound ligand encoding DNA is present. The amount of the target-bound ligand is determined by quantitative PCR. The degree of wash stringency can be monitored to a desired level and to very low detection levels for example to attomole levels. Nonspecific ligand binders may be competed out for example by adding wild type phage and designing primers that only amplify the ligand library. To prevent deterioration of signal-to-noise ratio, the sequences flanking the ligand encoding DNA may be changed frequently during rounds of selection. Sensitivity for the analysis of target-bound ligands may be controlled by changing target concentration, the number of PCR amplification cycles, the specificity of the PCR primers, and the detection method for PCR products.

Various inhibitory reactions of PCR may be alleviated by the addition of excipients including bovine serum albumin, cationic amines, and organic solvents and reference is made to Roux, (1995) "Optimization and Troubleshooting in PCR" in PCR Primer: A Laboratory Manual, Cold Spring Harbor Press. DMSO and glycerol may be used to improve amplification efficiency and specificity of PCR. The DNA of the target-bound ligand may also be extracted and purified using standard techniques.

To facilitate sequencing of desired clones or separation from undesired non-specific phage, the polynucleotide products generated by PCR may be labeled for example with biotinyl or fluorescent label moieties by incorporation during polymerase mediated catalysis. When the desired PCR product is to be cloned into a vector for additional rounds of selective targeting according to the method of the invention, it may be desirable to introduce diversity by mutagenic PCR methods, (See Stemmer, in Kay et al., supra). These include cassette mutagenesis, error prone PCR, DNA shuffling, ITCHY-SCRATCHY and the like as is well known by those in the art. Also reference is made to Tillett and Neilan, (1999) "Enzyme-free Cloning: A Rapid Method to Clone PCR Products Independent of Vector Restriction Enzyme Sites": Nucl. Acids. Res., 27:26e.

As mentioned above and as well known in the art, the PCR fragments may be cloned into various vectors for sequencing, they may be used in the formation of peptide protein fusions, or cloned into additional display vectors.

The target bound library members may also be identified preferably by mass spectrometric methods. This is a rapid and accurate identification of the structure of a compound based on the mass of the compound and on fragments of the compound generated in the mass spectrometry. The use of mass spectrometry to identify the structure of compounds has been reported in Cao et al., (1997) *Techniques in Protein Chemistry VIII*, Academic Press pages 177–184; and Youngquist et al., (1995) *J. Am. Chem. Soc.* 117:3900. Also reference is made to Cheng et al., (1995) *J. Am. Chem. Soc.*, 117:8859 and Walk et al., (1999) *Angew. Che. Int. Ed.*, 38:1763. One mass spectrometric technique is tandem mass spectrometry (MS/MS) wherein mass spectrometry is performed in tandem with liquid chromatography. To purify and separate the ligand of interest, this type of MS is preferably used to screen target-bound ligands other than phage-type peptides because of the need to separate and purify target-bound ligands from a biological system prior to injection of the ligands into a mass spectrometer. Various recently developed MS techniques are available for identification of the target-bound ligands. (See Wu et al., (1997) in *Chemistry and Biology*, vol. 14(9):653, Marshall et al., (1998), *Mass Spectrometry Reviews* 17:1, and Nelson et al., (1999) *J. Mol. Recognition*, 12:77).

Following the screening of one or more ligand members, particularly peptide ligands, the amino acid sequence of the peptides may be determined according to standard techniques known by those in the art such as direct amino acid sequencing of the selected peptide by using peptide sequencers, MS/MS, or manually or by determining the nucleotide sequence that encodes the peptide.

In a particular embodiment, the method concerns selecting peptides from a peptide library having a binding affinity for a target of between about $10^{-2}$M to about $10^{-15}$M and between about $10^{-2}$M to about $10^{-10}$M which comprises, contacting a peptide library with an anti-target to allow the peptides in the library to bind with the anti-target; separating unbound peptides from the anti-target bound peptides; contacting the separated unbound peptides with a target under conditions allowing binding of the unbound peptides with the target to form a target-bound peptide complex; separating the target-bound peptide complex from the peptides that do not bind to the target; and identifying the bound peptides on the target-bound peptide complex wherein the bound peptides are less than about 50 amino acids in length, are not antibodies, and have a selectivity in the range of about 2:1 to about 50:1. Preferably the target is skin or hair, and the anti-target is skin when the target is hair or the anti-target is hair when the target is skin. In one embodiment the bound peptides identified on the target-bound peptide complex are less than 25 amino acids in length with selectivity in the range of at least about 2:1 and also at least about 5:1.

Once the target-bound ligands are identified, the ligands may be exposed to repeated rounds of the selective targeting method and reference is made to FIG. 1. The target-bound ligands may be subject to diversification. Diversification including chemical diversity may include a number of mutagenesis techniques. See Saiki et al., (1988) *Science* 239:487; Zoller et al., (1982) *Nucl. Acids. Res.* 10:6487; and Smith (1985) *Ann Rev. Genetics.* 19:423. The target-bound ligands may be sequenced to determine the identity of the bound ligands and then oligonucleotides may be made based on the sequences but which include small variations. PCR may be used to make small changes in the nucleotide coding sequences for the ligands. This PCR mutagenesis can result in a mutation at any position in the coding sequence. Diversification may also take place by mutagenesis of a small subset of identified ligands. In general diversified ligands will have at least 80%, 85%, 90%, 95%, 97% or 99% sequence identity at the nucleotide level to the target-bound ligand. When the ligand is a peptide the diversified peptide will have at least 80%, 85%, 90%, 95%, 97% or 99% amino acid sequence identity to the identified target-bound peptide. The diversified ligands may be exposed to one or more rounds of the selective targeting method of the present invention. The diversified ligands may be screened with other identified target-bound ligands from which they were derived and assayed in appropriate applications for which the ligands were originally screened.

The selective targeting method of the current invention for screening a library of ligands that bind to a target has wide utility for many applications. In one particular application, the selective targeting method described herein may be used to identify ligands that bind to a target under harsh conditions. A harsh condition may include but is not limited to acidic pH, high temperature, and exposure to detergents, such as those found in household laundry detergents. In this respect, one exemplary application according to the invention is screening and identification of a ligand, particularly a peptide, which is useful in cleaning applications. Cleaning applications include but are not limited to detergent compositions, stain removal compositions, and textile treatment compositions. Particular stain targets include human body soil stain, a porphyrin derived stain, a tannin derived stain, a carotenoid pigment derived stain, an anthocyanin pigment derived stain, a soil-based stain, or an oil-based stain. Components of various cleaning compositions and particularly detergent compositions, are well known in the art and are not repeated herein. See for example the following references U.S. Pat. Nos. 3,929,678; 4,760,025; 4,800,197; 5,011,681; and *McCutheon's Detergents and Emulsifiers*, North American Edition (1986) Allured Publishing Co.

In a further application skin or hair binding peptides of the invention may be used in compositions for personal care applications. These compositions may take the form of lotions, creams, gels, sprays, shampoos and conditioners and the like.

Non-limiting examples of personal care applications which include a binding peptide of the invention are the following: a) using a skin binding peptide with an emollient which may result in the enhancement of the moisturizing properties of the emollient; b) combining a skin binding peptide with a bleaching or tanning agent which may result in the enhancement of skin bleaching or tanning properties; c) combining a skin binding peptides with a sunscreen for topical application; and d) combining a hair binding peptide with a dye or oxidizing agent wherein the hair coloring properties of the hair coloring formulation may be enhanced.

One skilled in the art is aware of various references including lists of cosmetic raw materials which may be used in personal care compositions. Two such references are *CTFA International Buyers' Guide*, 2002, Cosmetic, Toiletry and Fragrance Association, Washington D.C. and *CTFA International Cosmetic Ingredient Dictionary and Handbook*, 7th Ed. (1997) Vol. 2, Eds. Wenninger and McEwen, Cosmetic, Toiletry and Fragrance Association, Washington D.C. Also reference is made to WO 00/24372; WO 96/16630 and Sagarin, *Cosmetics, Science and Technology*, 2nd Ed. Vol. 1 (1972).

The selective targeting method and the ligands identified according to the method may be used in broad applications. In addition to the applications discussed herein above, other non-limiting applications, particularly for peptide ligands include: 1) for mapping antibody epitopes; 2) in providing new ligands for important binding molecules, such as enzymes and hormone receptors; 3) in providing potential agricultural compounds with pesticidial properties; 4) for developing new drug leads and exploiting current leads; 5) identifying industrial catalysts; 6) in identifying highly sensitive in vivo and in vitro diagnostic agents; 7) for increasing the efficiency of enzyme catalysts by binding metals and other cofactors; 8) for controlling protease action in vivo; 9) to change inhibitory properties of targeted proteins; 10) use in developing a targeted enzyme; 11) use in selective delivery of-gene therapy vectors to specific tissues or cell types; and 12) use in drug delivery or targeted actives.

Accordingly, the following examples are offered by way of illustration, and are not meant to limit the invention in any manner. Those skilled in the art will recognize or be able to ascertain using no more than routine experimentation, many equivalents to the specific embodiments of the invention described herein.

EXAMPLES

The procedures for restriction digest, ligation, preparation of competent cells using calcium chloride, preparation of 20 mg/ml isopropyl (IPTG), preparation of 20 mg/ml 5-bromo-4-chloro-3-indolyl-β-D-galactoside (X-gal), and preparation of phosphate-buffered saline (PBS) were according to well-known methods in the art and can be found in Sambrook et al. (1989) supra. Phage-displayed libraries (cyclic 7-mer, linear 7-mer and linear 12-mer) were supplied by New England Biolabs ((NEB; Beverly, Mass.). Restriction endonucleases EagI and Acc65I, 10× NEBuffer 3, T4 DNA ligase, alkaline calf intestinal phosphatase, *E. coli* ER2537 host strain, and M 13KE gIII cloning vector were supplied by NEB and used according to the manufacturer's instructions unless stated otherwise. Taq polymerase, 10× PCR Buffer, and dNTP mix were supplied by Roche Molecular Biochemicals (Indianapolis, Ind.). The HotStart Taq Master Mix kit for PCR came from Qiagen (Valencia, Calif.). PCR was carried out using a HYBAID Omn-E Thermocycler from E&K Scientific Products (Campbell, Calif.) or PTC 2000 DNA Engine™ from M.J. Research Inc. (Roche Molecular Systems, Inc. Alameda, Calif.). Nondenaturing polyacrylamide gels (8%) and D-15 DNA markers were obtained from Novex (San Diego, Calif.) and 2% E-gels and TOPO cloning kits were obtained from Invitrogen (Carlsbad, Calif.). Both the QIAquick Gel Extraction Kit and QIAquick PCR Purification Kit were obtained from QIAGEN (Valencia, Calif.). AmpliWax™ PCR Gems were obtained from Perkin Elmer (Boston, Mass.).

Example 1

Screening for Peptides Selected to Target Human Skin and Not Hair.

Two 3 inch strands of dark human hair (International Hair Importers & Products, White Plains, N.Y.) were placed in BSA blocked 50 ml conical tubes containing 10 ml of a 2% Neutrogena® Bath Gel (Neutrogena Corp.) solution in DI water. 10 µL of cyclic 7-mer or linear 12-mer peptide libraries ($10^{10}$ pfu/µl), or wild type phage ($10^9$ pfu/µl) were added and the samples mixed at room temperature for 15 min with rotatory shaking (30 rpm). The unbound supernatant was transferred to a new tube containing an additional two 3 inch strands of dark hair, and incubated at room temperature for 15 min with rotary shaking. After this second hair incubation, 500 µl of the solution was transferred to the surface of human skin tissues (EpiDerM™, MatTek Corp. Ashland, Mass.) in a 6 well culture plate containing 0.9 mL tissue culture media (MatTek Corp) for 30 minutes at room temperature with gentle agitation. The skin tissues were removed and washed 2× in 50 mls of 2% bath gel for 5 min each and 3× in 50 mls of PBS for 5 min each in blocked 50 mL conical tubes. After the final PBS wash, the skin tissues were frozen at −20° C. followed by PCR of the target bound ligand phage. A skin binding peptide identified according to this example containing a consensus sequence TQSL (SEQ ID NO: 119) is FTQSLPP (SEQ ID NO. 118).

Example 2

Pre-equilibrated skin tissues were placed into a 6 well culture plate containing fresh 0.9 mL tissue culture media and 300 µl of a 2% Neutrogena® Bath Gel containing, 10 µL of cyclic 7-mer or linear 12-mer peptide libraries ($10^{10}$ pfu/µl), or wild type phage ($10^9$ pfu/µl) were added to the skin surface. The samples were incubated at room temperature for 15 min with gentle agitation. The unbound supernatant was transferred to a new well containing skin tissue and the procedure was repeated. The incubation solution was transferred to nine 3 inch dark hair (International Hair Importers & Products, White Plains, N.Y.) strands in 50 ml tubes containing 10 ml of 2% body gel for 30 minutes at room temperature with rotatory shaking (30 rpm). The hair samples were then washed with 1×50 mls, 2×50 mls, or 4×50 mls of 2% bath gel; Wash cycles in PBS followed (1×25 mls for 5 min, 1×25 mls for 2 min, 2×50 mls for 5 min each, 150 mls total). After the final PBS wash, the hair samples containing bound phage peptides were frozen at −20° C. Hair binding peptides identified according to this example containing the consensus sequence LEST are LESTPKMK (SEQ ID NO. 115) and LESTPKM (SEQ ID NO. 7).

Example 3

Selection of Phage-Peptides that Bind to Hair or Skin Using PCR for Identification of High Affinity Phage-Peptide Clones.

The skin swatches and hair samples were frozen at −20° C. until PCR. In one example, PCR was performed directly on the hair and skin samples using the following conditions in 0.5 ml PCR tubes with the following reagents:
50 µl reaction mix (HotStart)
2 µl CB05 primer (25 µM)
2 µl CB12 primer (25 µM)
46 µl sterile dH$_2$O
5 µl of BSA at 10 mg/ml and 50 µl of mineral oil were added.
PCR amplification was performed post initiation at 95° C. for 15 min, using 30 cycles of denaturation at 94° C. for 30 sec, annealing at 58° C. for 30 sec and synthesis at 72° C. for 60 sec. Extension was preformed at 72° C. for 10 min. Primers were obtained from Operon Technologies, Inc. (Alameda, Calif.). The sequences of the primers were:

```
                                          SEQ ID NO. 122
CB05    CGTAGTGGCATTACGTATTTTACCCGTTTAATGG (5'-3')

SEQ ID NO. 123
CB12    CGAGAGGGTTGATATAAGTATAGCCCGGAATAGG (5'-3')

SEQ ID NO. 1
CB05    CGTAGTGGCATTACGTATTTTACCCGTTTAATGG (5'-3')

SEQ ID NO. 2
CB12    CGAGAGGGTTGATATAAGTATAGCCCGGAATAGG (5'-3')
```

Additionally 1 µl of the different PCR products was subjected to another round of PCR using the same program but the following ingredients were added:
50 µl reaction mix (HotStart)
1 µl CM13 01 primer (50 µM)
1 µl CM13 02 primer (50 µM)
47 µl sterile dH$_2$O
50 µl of BSA at 10 mg/ml and µl of mineral oil were added.
Primers were obtained from Operon Technologies, Inc. (Alameda, Calif.). The sequences for the primers were:

```
CM13 01
CCTCGAAAGCAAGCTGATAAACCG (5'-3')      SEQ ID NO. 124

CM13 02
CATTCCACAGACAACCCTCATAG (5'-3').      SEQ ID NO. 2
```

The PCR products were visualized on a 2% E-gel along with PCR products from dilutions of the various initial phage peptide libraries (positive control) and molecular weight markers, run under 65V for 40 min. 4 µl of the PCR products were subject to TOPO cloning and transformation according to standard protocol but all incubations were done for 30 minutes. The individual clones were submitted to PCR (12.5 µl Master Mix, 0.1 µl each of CM13 01 and CM13 02 primers, 12.3 µl sterile water per clone) using the same program as described above. Sequencing using 1 µl of PCR product and 11 µl of g96 primer was completed at Sequetech (Mountain View, Calif.); Biotech Core, Inc (Mountain View, Calif.) or internally using an ABI Applied Biosystem 373XL.

Example 4

Cloning of PCR Products.
PCR products from the first round of selection were cloned as follows:

Vector Preparation:
10 µg of M13KE vector (New England Biolabs (NEB), Beverly, Mass.) was digested overnight (16 h) at 37° C. and according to NEB recommended conditions, digestion was performed in 400 µl total volume as follows: M13KE,10 µl; Eag 1, 10 µl; Acc65 1, 10 µl; 10×NEB buffer 3, 40 µl; 100×BSA 4 µl; and dH$_2$O, 326 µl. The digested vector was purified using Qiagen PCR Purification Kit (Qiagen) using 30 µl of elution buffer (EB). The purified digest was stored at −20° C.

Insert Preparation:
PCR product from the first round of selection was purified using the Qiagen Purification Kit and eluted in 30 µl of EB buffer. 15 µl of the purified material was digested overnight in 100 µl total volume as follows: PCR product, 15 µl; Eag1, 1 µl; Acc651, 1 µl; 10×NEB buffer 3, 10 µl; 100×BSA, 1 µl; and dH$_2$O, 64µl. The digestion was followed by a heat shock treatment at 60° C. for 20 min and the product was stored at −20° C. until further use.

The ligation was performed as described below using the Takara kit at 16° C. for 30 min, then placed on ice. Vector preparation, 1 µl; Insert preparation, 1 µl; EB buffer, 3 µl; and Solution 1, 5 µl from Takara Biolnc., (Shiga, Japan).

Transformation:
5 µl of ligation mixture was used to transform 50 µl of TOP10F' chemically competent cells (Invitrogen) according to the commercial protocol. The cells were grown on LB plates overnight at 37° C.

The phage peptide libraries were amplified and titered according to standard techniques. Subsequent rounds of deselection and selection may also be performed according to the methods described above.

Example 5

Enzyme-linked Assay for Selective Binding of Peptides that Target Human Hair and Not Skin or Target Skin and Not Hair.

Peptide sequences identified in Examples 1 and 2 along with a random control peptide were C-terminally labeled with a linker molecule (biotinylated lysine) at the C-terminus (sequence GGGK SEQ ID NO: 125 (biotin)). In one specific example, the following sequences were used: the sequence LESTPKMK (SEQ ID NO. 115), which was screened on hair; the sequence FTQSLPR (SEQ ID NO. 116) which was screened on skin; and an activity control β-endorphin peptide YGGFMTSE (SEQ ID NO. 117).

Dark brown hair (3" long, 4 each), moistened with 2% Neutrogena® Bath Gel and pre-equilibrated human skin tissues obtained from MatTek, were placed in the wells of a 24 well plate. 1 ml of a 200 μM solution of the biotinylated peptide in 2% Neutrogena® Bath Gel was added to the hair and skin samples and incubated 30 min at room temperature with gentle agitation. The solution was then pipetted off and the hair and skin samples transferred with clean tweezers to a 50 ml conical tube, washed once with 50 ml of 2% bath gel, twice with 50 ml of water, and once with 50 ml of PBS. Each wash step took 5 min and was performed on a rotary shaker at 20 rpm. The hair and skin samples were transferred with clean tweezers to a fresh 24 well plate where 1 ml of streptavidin conjugated horseradish peroxidase (diluted 1/1000 in PBS) was added for 1 hr at room temperature under gentle rocking. Excess streptavidin HRP was removed by washing twice with 50 ml of PBS (5 min, 20 rpm each) in a 50 mL conical tube. The hair and skin samples were transferred to fresh wells and 1 ml of $H_2O_2$/OPD (45 ml of citrate buffer at pH 4.0, one tablet of 10 mg OPD (o-phenylene diamine, Sigma Cat. # P8287) then 76 μl of $H_2O_2$ at 30%) solution was added. The color was left to develop at room temperature. At various time intervals, 200 μl of solution from each tube was removed, placed into a 96 well MTP and absorbance was read at 430 nm. FIG. 2 shows that peptide binding is selective for the respective targets, relative to the control peptide.

What is claimed is:

1. An isolated hair binding peptide consisting of the amino acid sequence set forth in SEQ ID NO: 120.

* * * * *

```
                          SEQUENCE LISTING

<160> NUMBER OF SEQ ID NOS: 125

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
cctcgaaagc aagctgataa c                                             21

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
cattccacag acaaccctca tag                                           23

<210> SEQ ID NO 3
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 3

Arg Tyr Trp Gln Asp Ile Pro
1               5

<210> SEQ ID NO 4
<211> LENGTH: 7
<212> TYPE: PRT
<213> ORGANISM: Artificial Sequence
<220> FEATURE:
<223> OTHER INFORMATION: peptides screened from a phage display random
      peptide library
```

```
<400> SEQUENCE: 4

Ala Pro Glu Pro Ile Leu Ala
1               5

<210> SEQ ID NO 5
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 5

Asp Met Ile Met Val Ser Ile
1               5

<210> SEQ ID NO 6
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 6

Trp Thr Pro Lys Pro Thr Gln
1               5

<210> SEQ ID NO 7
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 7

Ala Thr Phe Pro Asn Gln Ser
1               5

<210> SEQ ID NO 8
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 8

Ala Ser Thr Val Gly Gly Leu
1               5

<210> SEQ ID NO 9
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 9

Thr Met Leu Pro Tyr Arg Pro
1               5

<210> SEQ ID NO 10
<211> LENGTH: 7
<212> TYPE: PRT
```

```
<213> ORGANISM: Artificial Sequence
<220> FEATURE:
<223> OTHER INFORMATION: peptides screened from a phage display random
      peptide library

<400> SEQUENCE: 10

Ala Trp His Ser Pro Ser Val
1               5

<210> SEQ ID NO 11
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 11

Leu Thr Gln Ser Phe Ser Ser
1               5

<210> SEQ ID NO 12
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 12

Thr His Lys Asn Thr Leu Arg
1               5

<210> SEQ ID NO 13
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 13

Gly Gln Thr His Phe His Val
1               5

<210> SEQ ID NO 14
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 14

Leu Pro Ile Leu Thr Gln Thr
1               5

<210> SEQ ID NO 15
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 15

Ser Ile Leu Pro Val Ser His
1               5
```

```
<210> SEQ ID NO 16
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 16

Leu Ser Gln Pro Ile Pro Ile
1               5

<210> SEQ ID NO 17
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 17

Gln Pro Leu Arg Lys Leu Pro
1               5

<210> SEQ ID NO 18
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 18

His Pro Ala Ser Gln Thr Phe Thr Phe Thr Arg Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 19

Asn Ser Asp Val Leu Phe Lys Pro Tyr Pro Met Phe
1               5                   10

<210> SEQ ID NO 20
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 20

Ser Ile Ser Ser Thr Pro Arg Ser Tyr His Trp Thr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: peptides screened from a phage display random
      peptide library
```

```
<400> SEQUENCE: 21

Thr Pro Ser Thr Met Pro Pro Ser Leu Pro Leu Arg
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 22

Thr Pro Asp Lys Asp Thr Met Ser Pro Pro Val Pro
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 23

His Leu Pro Val Arg Ile Thr Asp Trp Phe His His
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 24

Glu Pro Ile Leu Met Arg Ala Ser Pro Phe Arg Glu
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 25

Glu Ser Ser Ala Phe Thr Ala Leu Ser Gly Gln Pro
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 26

Ser Ser Pro Asn Met Ile Thr Leu Leu Ser Ser Leu
 1               5                  10

<210> SEQ ID NO 27
<211> LENGTH: 12
```

```
<212> TYPE: PRT
<213> ORGANISM: Artificial Sequence
<220> FEATURE:
<223> OTHER INFORMATION: peptides screened from a phage display random
      peptide library

<400> SEQUENCE: 27

His Thr Phe Gln His Gln Trp Thr His Gln Thr Arg
 1               5                  10

<210> SEQ ID NO 28
<211> LENGTH: 14
<212> TYPE: PRT
<213> ORGANISM: Artificial Sequence
<220> FEATURE:
<223> OTHER INFORMATION: peptides screened from a phage display random
      peptide library

<400> SEQUENCE: 28

Gly Gly His Thr Phe Gln His Gln Trp Thr His Gln Thr Arg
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 29

His Pro Ser Trp Ala Pro Val Ser Ser Thr Leu Arg
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 30

Ser Thr Pro His Gln Pro Cys Ala Thr Ala Pro His
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 31

Leu Asp Gln Ile Leu Thr Ser Ser Arg Ile Trp Pro
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 32

His Tyr Leu Lys Asn Val Glu Ala Thr Gly Pro Arg
```

```
<210> SEQ ID NO 33
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 33

Ser Ser Arg Met Tyr Pro Ser Pro Asp Ser Phe Met
1               5                   10

<210> SEQ ID NO 34
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 34

Ser Met Ala Thr Gln Leu Gln Gly Asn Ile Thr Met
1               5                   10

<210> SEQ ID NO 35
<211> LENGTH: 11
<212> TYPE: PRT
<213> ORGANISM: Artificial Sequence
<220> FEATURE:
<223> OTHER INFORMATION: peptides screened from a phage display random
      peptide library

<400> SEQUENCE: 35

Tyr Met His Ala Ser Leu Met Trp Ala Phe Gly
1               5                   10

<210> SEQ ID NO 36
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 36

Lys Ala Leu Pro Pro Asn Ser Thr Leu Ser Arg Ala
1               5                   10

<210> SEQ ID NO 37
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 37

Leu Glu Leu Pro Asn Asn Ile Gln Ser Ile Thr Ser
1               5                   10

<210> SEQ ID NO 38
<211> LENGTH: 12
<212> TYPE: PRT
<213> ORGANISM: Artificial Sequence
<220> FEATURE:
<223> OTHER INFORMATION: peptides screened from a phage display random
```

```
            peptide library

<400> SEQUENCE: 38

Gln Val Phe His Ile Ala Gly Val Arg Asp Gln Val
1               5                   10

<210> SEQ ID NO 39
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 39

Arg Glu Pro Ala Pro Ser Cys Thr Thr Thr Cys Leu
1               5                   10

<210> SEQ ID NO 40
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 40

Tyr Pro His His Pro Arg Leu His Tyr Thr Phe Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 41

Lys Val Thr Glu Phe Gln Lys Ala His Cys Ser Ser
1               5                   10

<210> SEQ ID NO 42
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 42

Gly Ile Thr Leu His Asn Thr Met Val Pro Trp Thr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 43

Glu Ala Gly Leu Ser Pro Thr Arg Pro Tyr Met Phe
1               5                   10

<210> SEQ ID NO 44
```

```
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 44

Ser His His Thr His Tyr Gly Gln Pro Gly Pro Val
1               5                   10

<210> SEQ ID NO 45
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 45

Phe Tyr Pro Ser Pro Ser Thr Ala Lys Met Trp Arg
1               5                   10

<210> SEQ ID NO 46
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 46

Ser Gly Phe Gln Ser Ala Tyr Ala Phe Pro Tyr Ser
1               5                   10

<210> SEQ ID NO 47
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 47

Met Val Ser Gln Pro Asp Pro Arg Ala Thr Leu Arg
1               5                   10

<210> SEQ ID NO 48
<211> LENGTH: 12
<212> TYPE: PRT
<213> ORGANISM: Artificial Sequence
<220> FEATURE:
<223> OTHER INFORMATION: peptides screened from a phage display random
      peptide library
<220> FEATURE:
<221> NAME/KEY: VARIANT
<222> LOCATION: (1)...(12)
<223> OTHER INFORMATION: Xaa = Any Amino Acid
<220> FEATURE:
<221> NAME/KEY: VARIANT
<222> LOCATION: (1)...(12)
<223> OTHER INFORMATION: Xaa = Any Amino Acid

<400> SEQUENCE: 48

Ile Lys Ser Lys Ile Leu Ile Pro Xaa Ser Ala Pro
1               5                   10

<210> SEQ ID NO 49
<211> LENGTH: 12
```

```
<212> TYPE: PRT
<213> ORGANISM: Artificial Sequence
<220> FEATURE:
<223> OTHER INFORMATION: peptides screened from a phage display random
      peptide library

<400> SEQUENCE: 49

Thr Asn Val Ser Thr Gln Asn Ile Val Gln Pro Leu
1               5                   10

<210> SEQ ID NO 50
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 50

Leu Ser Pro His Leu Ala Arg
1               5

<210> SEQ ID NO 51
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 51

Thr His Arg Pro Asp Trp Asp
1               5

<210> SEQ ID NO 52
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 52

Ala Pro Lys Ser Phe Lys Thr
1               5

<210> SEQ ID NO 53
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 53

Ala Tyr Ser Gln Trp Lys Tyr
1               5

<210> SEQ ID NO 54
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 54

Asp Phe Ser Pro Gln Leu Asp
```

-continued

```
1               5

<210> SEQ ID NO 55
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 55

Gly Leu Phe Glu Trp Arg Val
1               5

<210> SEQ ID NO 56
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 56

Ile Leu Asn His Pro Pro Asn
1               5

<210> SEQ ID NO 57
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 57

Leu Asn Gln Lys Asn Val Thr
1               5

<210> SEQ ID NO 58
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 58

Leu Pro Ser Glu Phe Leu Arg
1               5

<210> SEQ ID NO 59
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 59

Met Pro Gly Ala Thr Ser Leu
1               5

<210> SEQ ID NO 60
<211> LENGTH: 7
<212> TYPE: PRT
<213> ORGANISM: Artificial Sequence
<220> FEATURE:
<223> OTHER INFORMATION: peptides screened from a phage display random
```

-continued

```
                peptide library

<400> SEQUENCE: 60

Gln Met Ser Ala Gln Trp Arg
  1               5

<210> SEQ ID NO 61
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 61

Ser Asn Thr Ala Ile Trp Arg
  1               5

<210> SEQ ID NO 62
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 62

Thr Ala Ser Pro Met Pro Leu
  1               5

<210> SEQ ID NO 63
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 63

Val Ala Leu Pro Thr Leu Thr
  1               5

<210> SEQ ID NO 64
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 64

Leu Asp Tyr Lys His Asp Leu
  1               5

<210> SEQ ID NO 65
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 65

Ser Ala Ala Ala Asp Tyr Leu
  1               5

<210> SEQ ID NO 66
```

```
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 66

Thr Pro Gly Pro Leu Phe Leu
1               5

<210> SEQ ID NO 67
<211> LENGTH: 7
<212> TYPE: PRT
<213> ORGANISM: Artificial Sequence
<220> FEATURE:
<223> OTHER INFORMATION: peptides screened from a phage display random
      peptide library
<220> FEATURE:
<221> NAME/KEY: VARIANT
<222> LOCATION: (1)...(7)
<223> OTHER INFORMATION: Xaa = Any Amino Acid
<220> FEATURE:
<221> NAME/KEY: VARIANT
<222> LOCATION: (1)...(7)
<223> OTHER INFORMATION: Xaa = Any Amino Acid

<400> SEQUENCE: 67

Asp Xaa Gln Asp Asn Ile Trp
1               5

<210> SEQ ID NO 68
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 68

Met Pro Gln Pro Ser Ser Met
1               5

<210> SEQ ID NO 69
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 69

Leu Thr Ile Thr Ile Gln Glu
1               5

<210> SEQ ID NO 70
<211> LENGTH: 7
<212> TYPE: PRT
<213> ORGANISM: Artificial Sequence
<220> FEATURE:
<223> OTHER INFORMATION: peptides screened from a phage display random
      peptide library
<220> FEATURE:
<221> NAME/KEY: VARIANT
<222> LOCATION: (1)...(7)
<223> OTHER INFORMATION: Xaa = Any Amino Acid
<220> FEATURE:
<221> NAME/KEY: VARIANT
<222> LOCATION: (1)...(7)
<223> OTHER INFORMATION: Xaa = Any Amino Acid
```

```
<400> SEQUENCE: 70

Xaa Pro Gly Pro Leu Phe Leu
 1               5

<210> SEQ ID NO 71
<211> LENGTH: 7
<212> TYPE: PRT
<213> ORGANISM: Artificial Sequence
<220> FEATURE:
<223> OTHER INFORMATION: peptides screened from a phage display random
      peptide library
<220> FEATURE:
<221> NAME/KEY: VARIANT
<222> LOCATION: (1)...(7)
<223> OTHER INFORMATION: Xaa = Any Amino Acid
<220> FEATURE:
<221> NAME/KEY: VARIANT
<222> LOCATION: (1)...(7)
<223> OTHER INFORMATION: Xaa = Any Amino Acid

<400> SEQUENCE: 71

Thr Asn Phe Ala Thr Xaa Leu
 1               5

<210> SEQ ID NO 72
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 72

Asp Ala Arg Asn Ala Leu Phe
 1               5

<210> SEQ ID NO 73
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 73

Trp Thr Ser Leu Ile Ser Asn
 1               5

<210> SEQ ID NO 74
<211> LENGTH: 10
<212> TYPE: PRT
<213> ORGANISM: Artificial Sequence
<220> FEATURE:
<223> OTHER INFORMATION: peptides screened from a phage display random
      peptide library
<220> FEATURE:
<221> NAME/KEY: VARIANT
<222> LOCATION: (1)...(10)
<223> OTHER INFORMATION: Xaa = Any Amino Acid
<220> FEATURE:
<221> NAME/KEY: VARIANT
<222> LOCATION: (1)...(10)
<223> OTHER INFORMATION: Xaa = Any Amino Acid

<400> SEQUENCE: 74

Ala Cys Trp Leu Arg Pro Xaa Leu His Cys
 1               5                  10

<210> SEQ ID NO 75
```

```
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 75

Asn Leu Ser Ser Ser Asn Lys His Ala Val Gly Asn
1               5                   10

<210> SEQ ID NO 76
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 76

Tyr Val His Arg Pro Asn Ala
1               5

<210> SEQ ID NO 77
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 77

Gly Ser Tyr Asp Pro Lys Glu Phe His His Pro Gln
1               5                   10

<210> SEQ ID NO 78
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 78

Asn Phe Phe Pro Thr Trp Ile Leu Pro Glu His Thr
1               5                   10

<210> SEQ ID NO 79
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 79

Cys Ser Lys His Ser Gln Ile Thr Cys
1               5

<210> SEQ ID NO 80
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 80
```

-continued

```
Cys Lys Thr Asn Pro Ser Gly Ser Cys
 1               5

<210> SEQ ID NO 81
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 81

Cys Arg Pro Thr Gly His Ser Leu Cys
 1               5

<210> SEQ ID NO 82
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 82

Cys Lys His Ser Ala Lys Ala Glu Cys
 1               5

<210> SEQ ID NO 83
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 83

Cys Lys Pro Ser Ser Ala Ser Ser Cys
 1               5

<210> SEQ ID NO 84
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 84

Cys Pro Val Thr Lys Arg Val His Cys
 1               5

<210> SEQ ID NO 85
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 85

Cys Thr Leu His Trp Trp Val Thr Cys
 1               5

<210> SEQ ID NO 86
<211> LENGTH: 9
<212> TYPE: PRT
<213> ORGANISM: Artificial Sequence
<220> FEATURE:
```

```
<223> OTHER INFORMATION: peptides screened from a phage display random
      peptide library

<400> SEQUENCE: 86

Cys Pro Tyr Lys Ala Ser Phe Tyr Cys
 1               5

<210> SEQ ID NO 87
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 87

Cys Pro Leu Arg Thr Ser His Thr Cys
 1               5

<210> SEQ ID NO 88
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 88

Cys Glu Ala Thr Pro Arg Asp Thr Cys
 1               5

<210> SEQ ID NO 89
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 89

Cys Asn Pro Leu His Thr Leu Ser Cys
 1               5

<210> SEQ ID NO 90
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 90

Cys Lys His Glu Arg Ile Trp Ser Cys
 1               5

<210> SEQ ID NO 91
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 91

Cys Ala Thr Asn Pro Pro Pro Met Cys
 1               5
```

<210> SEQ ID NO 92
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 92

Cys Ser Thr Thr Ser Pro Asn Met Cys
 1               5

<210> SEQ ID NO 93
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 93

Cys Ala Asp Arg Ser Phe Arg Tyr Cys
 1               5

<210> SEQ ID NO 94
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 94

Cys Pro Lys Ala Asp Ser Lys Gln Cys
 1               5

<210> SEQ ID NO 95
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 95

Cys Pro Asn Gln Ser His Leu His Cys
 1               5

<210> SEQ ID NO 96
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 96

Cys Ser Gly Ser Glu Thr Trp Met Cys
 1               5

<210> SEQ ID NO 97
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 97

Cys Ala Leu Ser Ala Pro Tyr Ser Cys
1               5

<210> SEQ ID NO 98
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 98

Cys Lys Met Pro Thr Ser Lys Val Cys
1               5

<210> SEQ ID NO 99
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 99

Cys Ile Thr Pro Lys Arg Pro Tyr Cys
1               5

<210> SEQ ID NO 100
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 100

Cys Lys Trp Ile Val Ser Glu Thr Cys
1               5

<210> SEQ ID NO 101
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 101

Cys Pro Asn Ala Asn Ala Pro Ser Cys
1               5

<210> SEQ ID NO 102
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 102

Cys Asn Val Gln Ser Leu Pro Leu Cys
1               5

<210> SEQ ID NO 103
<211> LENGTH: 9
<212> TYPE: PRT
<213> ORGANISM: Artificial Sequence

```
<220> FEATURE:
<223> OTHER INFORMATION: peptides screened from a phage display random
      peptide library

<400> SEQUENCE: 103

Cys Tyr Asn Leu Tyr Gly Trp Thr Cys
1               5

<210> SEQ ID NO 104
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 104

Cys Thr Leu Trp Pro Thr Phe Trp Cys
1               5

<210> SEQ ID NO 105
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 105

Cys Asn Leu Trp Pro His Phe Trp Cys
1               5

<210> SEQ ID NO 106
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 106

Cys Ser Leu Trp Pro Ala Phe Trp Cys
1               5

<210> SEQ ID NO 107
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 107

Cys Ser Leu Trp Pro His Phe Trp Cys
1               5

<210> SEQ ID NO 108
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 108

Cys Ala Pro Trp Asn Ser His Ile Cys
1               5
```

```
<210> SEQ ID NO 109
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 109

Cys Ala Pro Trp Asn Leu His Ile Cys
 1               5

<210> SEQ ID NO 110
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 110

Cys Leu Pro Ser Trp His Leu Arg Cys
 1               5

<210> SEQ ID NO 111
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 111

Cys Pro Thr Ile Leu Glu Trp Tyr Cys
 1               5

<210> SEQ ID NO 112
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 112

Cys Thr Leu Tyr Pro Gln Phe Trp Cys
 1               5

<210> SEQ ID NO 113
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 113

Cys His Leu Ala Pro Ser Ala Val Cys
 1               5

<210> SEQ ID NO 114
<211> LENGTH: 13
<212> TYPE: PRT
<213> ORGANISM: Artificial Sequence
<220> FEATURE:
<223> OTHER INFORMATION: peptides screened from a phage display random
      peptide library
```

```
<400> SEQUENCE: 114

Gly Ser Ile Ser Ser Thr Pro Arg Ser Tyr His Trp Thr
 1               5                  10

<210> SEQ ID NO 115
<211> LENGTH: 8
<212> TYPE: PRT
<213> ORGANISM: Artificial Sequence
<220> FEATURE:
<223> OTHER INFORMATION: peptides screened from a phage display random
      peptide library

<400> SEQUENCE: 115

Leu Glu Ser Thr Pro Lys Met Lys
 1               5

<210> SEQ ID NO 116
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 116

Phe Thr Gln Ser Leu Pro Arg
 1               5

<210> SEQ ID NO 117
<211> LENGTH: 8
<212> TYPE: PRT
<213> ORGANISM: Artificial Sequence
<220> FEATURE:
<223> OTHER INFORMATION: peptides screened from a phage display random
      peptide library

<400> SEQUENCE: 117

Tyr Gly Gly Phe Met Thr Ser Glu
 1               5

<210> SEQ ID NO 118
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 118

Phe Thr Gln Ser Leu Pro Pro
 1               5

<210> SEQ ID NO 119
<211> LENGTH: 4
<212> TYPE: PRT
<213> ORGANISM: Artificial Sequence
<220> FEATURE:
<223> OTHER INFORMATION: consensus sequence

<400> SEQUENCE: 119

Thr Gln Ser Leu
 1

<210> SEQ ID NO 120
<211> LENGTH: 7
<212> TYPE: PRT
<213> ORGANISM: Artificial Sequence
```

```
<220> FEATURE:
<223> OTHER INFORMATION: peptides screened from a phage display random
      peptide library

<400> SEQUENCE: 120

Leu Glu Ser Thr Pro Lys Met
 1               5

<210> SEQ ID NO 121
<211> LENGTH: 4
<212> TYPE: PRT
<213> ORGANISM: Artificial Sequence
<220> FEATURE:
<223> OTHER INFORMATION: consensus sequence

<400> SEQUENCE: 121

Leu Glu Ser Thr
 1

<210> SEQ ID NO 122
<211> LENGTH: 34
<212> TYPE: DNA
<213> ORGANISM: Artificial Sequence
<220> FEATURE:
<223> OTHER INFORMATION: primer

<400> SEQUENCE: 122
cgtagtggca ttacgtattt tacccgttta atgg                          34

<210> SEQ ID NO 123
<211> LENGTH: 34
<212> TYPE: DNA
<213> ORGANISM: Artificial Sequence
<220> FEATURE:
<223> OTHER INFORMATION: primer

<400> SEQUENCE: 123
cgagagggtt gatataagta tagcccggaa tagg                          34

<210> SEQ ID NO 124
<211> LENGTH: 24
<212> TYPE: DNA
<213> ORGANISM: Artificial Sequence
<220> FEATURE:
<223> OTHER INFORMATION: primer

<400> SEQUENCE: 124
cctcgaaagc aagctgataa accg                                     24

<210> SEQ ID NO 125
<211> LENGTH: 4
<212> TYPE: PRT
<213> ORGANISM: Artificial Sequence
<220> FEATURE:
<223> OTHER INFORMATION: peptide assay sequence

<400> SEQUENCE: 125

Gly Gly Gly Lys
 1
```